(12) United States Patent
Hyatt et al.

(10) Patent No.: US 7,697,997 B2
(45) Date of Patent: Apr. 13, 2010

(54) MULTIFUNCTION ELECTRODE PAD

(75) Inventors: Christopher Hyatt, Syracuse, NY (US); Arthur Eddy, Jr., Hampton, NH (US)

(73) Assignee: ConMed Corporation, Utica, NY (US)

( * ) Notice: Subject to any disclaimer, the term of this patent is extended or adjusted under 35 U.S.C. 154(b) by 1036 days.

(21) Appl. No.: 11/328,930

(22) Filed: Jan. 10, 2006

(65) Prior Publication Data

US 2007/0162099 A1 Jul. 12, 2007

(51) Int. Cl.
*A61N 1/18* (2006.01)
(52) U.S. Cl. .................................. 607/142; 607/152
(58) Field of Classification Search ........................ None
See application file for complete search history.

(56) References Cited

U.S. PATENT DOCUMENTS

| | | | |
|---|---|---|---|
| 4,494,552 A | 1/1985 | Heath | |
| 4,592,961 A | 6/1986 | Ehrreich | |
| 4,895,169 A | 1/1990 | Heath | |
| 5,080,099 A | 1/1992 | Way et al. | |
| 5,571,165 A | * 11/1996 | Ferrari | ........................ 607/142 |
| 5,733,324 A | * 3/1998 | Ferrari | ........................ 607/152 |
| 5,824,033 A | * 10/1998 | Ferrari | ........................ 607/142 |
| 5,843,342 A | 12/1998 | Ehrreich | |
| 6,600,957 B2 | 7/2003 | Gadsby | |
| 2001/0031988 A1 | 10/2001 | Kurata et al. | |
| 2003/0004558 A1 | 1/2003 | Gadsby | |

FOREIGN PATENT DOCUMENTS

EP 0 778 046 6/1997

\* cited by examiner

*Primary Examiner*—Carl H. Layno
*Assistant Examiner*—Jon-Eric C. Morales
(74) *Attorney, Agent, or Firm*—Marjama Muldoon Blasiak & Sullivan LLP

(57) ABSTRACT

A multifunction electrode (MFE) pad, which includes a multi-strand conductor having one end in the form of dispersed carbon fibers, and another end adapted for connection to a defibrillation unit. A conductive substrate is in electrical communication with one end of the multi-strand conductor. The conductive substrate includes a conductive back side, an intermediate conductive polymer layer, and a conductive front side, the front side being a metal/metal chloride coating containing at least 25% by weight of metal chloride. The MFE pad further includes a conductive hydrogel layer covering said front side of the conductive substrate and a backing layer covering one end of the multi-strand conductor and the back side of the conductive substrate. The backing layer has a surface area that is greater than the surface area of the conductive hydrogel layer.

12 Claims, 7 Drawing Sheets

MULTIFUNCTION ELECTRODE PAD

FIELD OF THE INVENTION

The present invention relates to the field of electrodes used by heath care providers to provide electrical current to stimulate a heartbeat and to receive changes of electrical potential occurring during the heartbeat.

BACKGROUND OF THE INVENTION

Multifunction Electrode (MFE) pads are widely used in the treatment and diagnosis of cardiac ailments. Health care professionals and other first-aid providers use MFE pads to monitor the electrical potential during a heartbeat, to provide high-energy electrical stimulation for defibrillation, and to provide lower level electrical stimulation for pacing. Prior to the development of such pads, care providers were required to apply multiple types of pads and possibly use other means of transferring electric current to the patient (i.e., paddles). As one can easily imagine, the use of multiple electrodes along with the use of other devices leads to potential errors and further injury when implemented during an emergency situation.

The creation of a true MFE pad requires designers to balance many factors, not the least of which is price, since the pads are single-use only. A modern MFE pad must be able to transfer short bursts of significant electrical energy while being able to dissipate such energy quickly so that monitoring remains unaffected. MFE pads must also evenly distribute energy across the surface of the pad to reduce the likelihood of burning a patient wearing the pad. Additionally, MFE pads must remain transparent to x-ray transmissions to allow for diagnostic imaging without removal of the pads.

MFE pads contain at least three layers used to effect the transfer of electrical energy between an electrical device and the patient. An electrode layer is located between a layer of protective outer foam and a layer of conductive gel. The conductive gel ensures contact between the electrode layer and the patient's body. The layer of foam, sized to be larger than the electrode layer, is added to cover the electrode and gel layers. The added size allows the foam to extend beyond the periphery of the other two layers to insulate and protect the electrode and gel layers while adding additional adhesive capacity around the periphery of the pad.

The conductive gel spans the distance between the electrode layer and the patient's body. The gel functions to wet the patient's skin making it more accepting to the flow of electrical energy. The physical properties of the gel also help to ensure contact over the entire surface of the exposed gel to distribute the energy being transferred. Lastly, the gel functions as an adhesive helping to ensure that distributed contact with the patient is maintained.

The electrode layer often includes a metal/metal chloride film adhered to a carbon-filled polymer sheet, which is typically a carbon-filled polyvinyl chloride (PVC). The sheet helps to support the metal/metal chloride film. The metal is the primary conductor of the electric energy across the pad while the chloride of the metal allows for the conduction of electrical energy from the electrode to the gel.

The ability of an MFE pad to dissipate energy quickly has come under significant scrutiny. The American National Standards Institute (ANSI) along with the Association for the Advancement of Medical Instrumentation (AAMI) publishes standards for the testing and performance of MFE pads. In particular, a standard known as ANSI/AAMI DF2:1996 was developed to standardize the performance testing of MFE pads and to provide target or allowable limits for the accumulation of DC offset potential measured across a pair of MFE pads.

A measure of an MFE pad's DC offset potential is a measure of the pad's ability to provide energy transfer while retaining the capability to monitor. Electrode pairs store energy by effectively forming a capacitor with the metal layer forming one plate of the capacitor, the human body forming another plate of the capacitor, and the hydrogel forming the dielectric material between the plates. This energy buildup can be seen as a residual voltage between periods of electric energy transfer from the electrode to the patient. This residual voltage or "DC offset potential" has a negative effect of skewing or masking electric signals being generated by the patient's nervous system being monitored through the electrode. Therefore, the lower the DC offset potential the better.

ANSI/AAMI DF2:1996 requires that the DC offset potential across a pair of MFE pads remain less than 400 mV during 60 minutes of pacing, where pacing includes 170, 20 millisecond pulses of 200 mA every minute. While most of the pads currently available continue to fail this standard, one pad, a Philips M3718A, appears to meet these requirements. The construction of this MFE pad is disclosed in U.S. Pat. No. 6,600,957, the entirety of which is incorporated herein by reference.

Current knowledge in the art indicates that the only way to meet the requirements of ANSI/AAMI DF2:1996 is to make the layer extremely thick when compared to others in the prior art. For example, U.S. Pat. No. 6,600,957, discloses that the metal/metal chloride coating of a successful MFE pad design must be "considerably thicker by a factor of six in order to enable the electrode to meet certain pacing requirements which the prior devices are unable to meet." This metal/metal chloride film of the electrode layer is very expensive to create and apply. Therefore, MFE pads containing such thick layers are very costly, especially for a disposable item.

The current financial crisis affecting the medical care systems around the world can hardly afford the use of expensive MFE pads incorporating a larger amount of expensive components, especially in a disposable product. However, heath care providers should be able to purchase MFE pads that meet the standards currently outlined in ANSI/AAMI DF2:1996 for the safety it offers to the people in need of safe cardiac treatment and care. To date, no such low-cost MFE pad is available.

SUMMARY OF THE INVENTION

It is an object of the present invention to provide a multifunction electrode (MFE) pad that meets the safety standards outlined in ANSI/AAMI DF2:1996 while remaining sufficiently cost effective.

In one embodiment of the invention, the MFE pad includes a multi-strand conductor having one end in the form of dispersed carbon fibers, and another end adapted for connection to a defibrillation unit. A conductive substrate is in electrical communication with one end of the multi-strand conductor. The conductive substrate includes a conductive back side, an intermediate conductive polymer layer, and a conductive front side. The front side is a metal/metal chloride coating containing at least 25% by weight of metal chloride. A conductive hydrogel layer covers the front side of the conductive substrate. A backing layer covers the one end of the multi-strand conductor and the back side of the conductive substrate. The backing layer has a surface area that is greater than the surface area of the conductive hydrogel layer.

Preferably, the metal chloride is present in the metal/metal chloride coating in an amount of not more than 45% by weight. Even more preferably, the metal chloride is present in the metal/metal chloride coating in an amount of 30%-40% by weight. Most preferably, the metal chloride is present in the metal/metal chloride coating in an amount of 35% by weight. It is also preferable that the thickness of the front side of the conductive substrate range from about 0.6 to about 1.0 mils.

In accordance with another embodiment of the present invention, the metal/metal chloride coating contains a mixture of metal particles and metal chloride particles. Preferably, the metal particles comprise silver and the metal chloride particles comprise silver chloride.

In accordance with another embodiment of the present invention, the conductive back side of the conductive substrate has a thickness of about 0.3 to about 1.0 mils. Preferably, the back side is a metal/metal chloride coating. As an alternative, the conductive back side can be a metal foil. For ease of manufacture, the composition of the conductive back side can be the same as the composition of the conductive front side.

In another embodiment of the invention, a stacked laminate includes first and second multifunction electrodes as described above, which are positioned such that the conductive hydrogel of the first multifunction electrode faces the conductive hydrogel of the second multifunction electrode. A release layer has first and second sides on which the conductive hydrogel layers of the first and second multifunction electrodes are adhered, respectively. The backing layers of the first and second multifunction electrodes are also adhered to the first and second sides of the release layer to seal the conductive hydrogel layers from the environment. This embodiment is particularly useful, as the MFE pads are almost always used in pairs.

BRIEF DESCRIPTION OF THE DRAWINGS

For a full understanding of the nature and objects of the invention, reference should be made to the following detailed description of a preferred mode of practicing the invention, read in connection with the accompanying drawings in which.

DETAILED DESCRIPTION OF THE INVENTION

Figure 1:
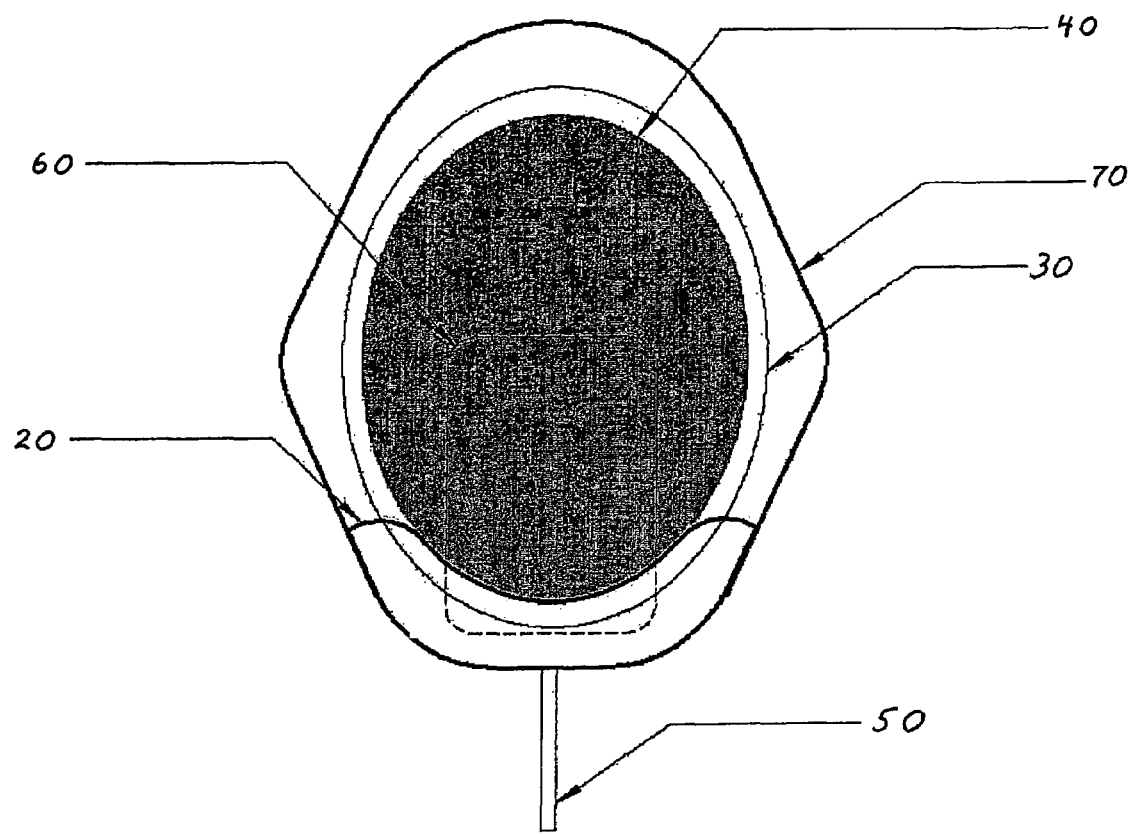
FIG. 1 is a plan view of a multifunction electrode pad in accordance with one embodiment of the present invention.
Figure 2:
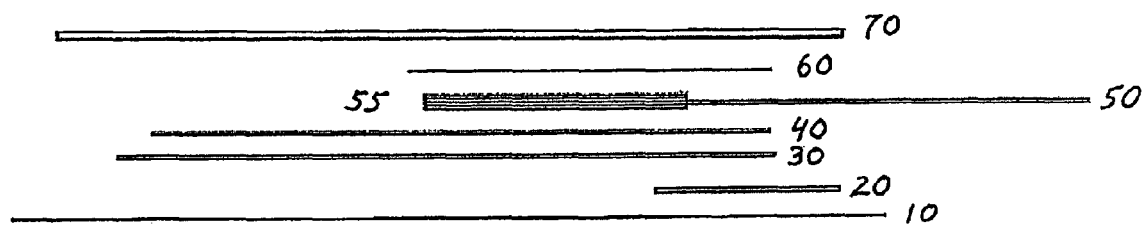
FIG. 2 is an exploded side view of a multifunction electrode pad in accordance with one embodiment of the present invention.

A plan view of a preferred embodiment of a Multifunction Electrode (MFE) pad according to the present invention is illustrated in FIG. 1. The MFE pad will be discussed in greater detail in a manner, which follows the path of electrical energy as it flows through the MFE pad to a patient's body. Even though this is the electrical path taken for purposes of clarity to a reader, it should be well understood that MFE pads are bi-directional in terms of electrical energy. For example, a pad that functions as an anode (positive current into a patient) may also function to receive electrical signals from biological sources of energy within the patient.

Electrical energy can travel to an MFE pad via a conductive wire 50. The conductive wire 50 can be made of any known conductor. However, the conductor material must be selected based on a desired amount of X-ray transparency. X-ray transparency is defined as the quality of being substantially invisible at X-ray irradiation levels routinely used to create images of the patient's chest. If X-ray transparency is not desired, a multi-strand conductor made of metal can be utilized.

Figure 3:
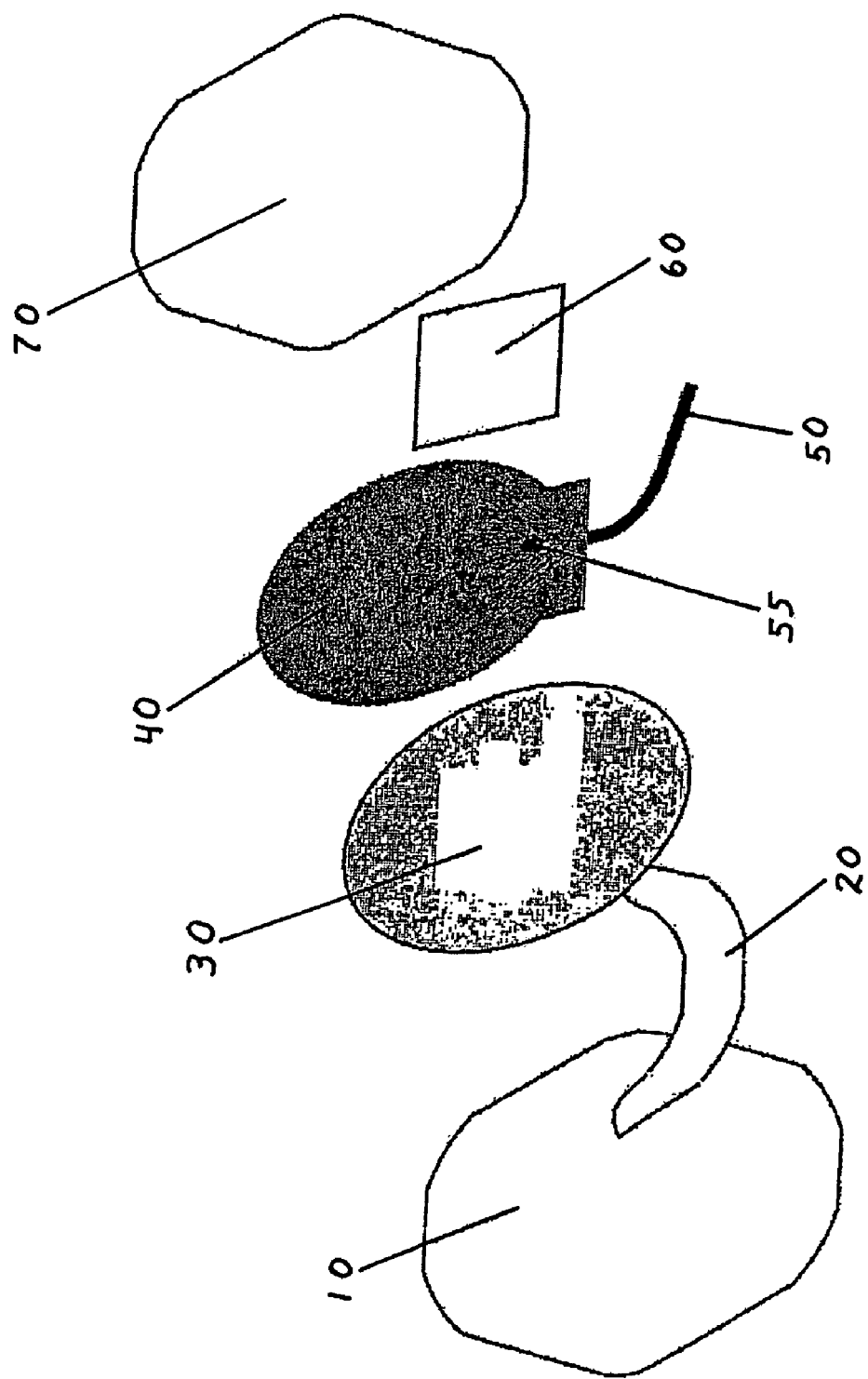
FIG. 3 is an exploded perspective view of a multifunction electrode pad in accordance with one embodiment of the present invention.

A multi-strand conductive wire 50 is preferable because it allows the individual strands of the conductor to be spread out in a fan shape 55 (FIG. 3) across a conductive substrate 40 to better disperse the transfer of electrical energy. If X-ray transparency is desired, as in the present case, a carbon fiber tow is preferably used. In the present embodiment, the conductive wire 50 is an X-ray transparent carbon fiber tow including nickel coated carbon fibers. The conductive wire 50 preferably has between 300 and 1200 fibers, each fiber having a nickel coating being 20% to 50% by weight of the fiber. The greater the number of fibers and the greater the percentage of plating increases the amount of electrical energy that can potentially be carried by the conductive wire 50. The conductive wire 50 according to this description can be purchased from Minnesota Wire and Cable.

The conductive wire fan 55 is electrically attached to a back side 120 (FIG. 4) of the conductive substrate 40 using a wire fan adhesive 60. The wire fan adhesive 60 is preferably a 5 mil semi-rigid polyethylene sheet having an acrylic adhesive. Depending on the type of materials used in the conductive wire 50, several other attachment methods may be utilized including the use of metal fittings and fasteners as is well known in the art.

Figure 4:
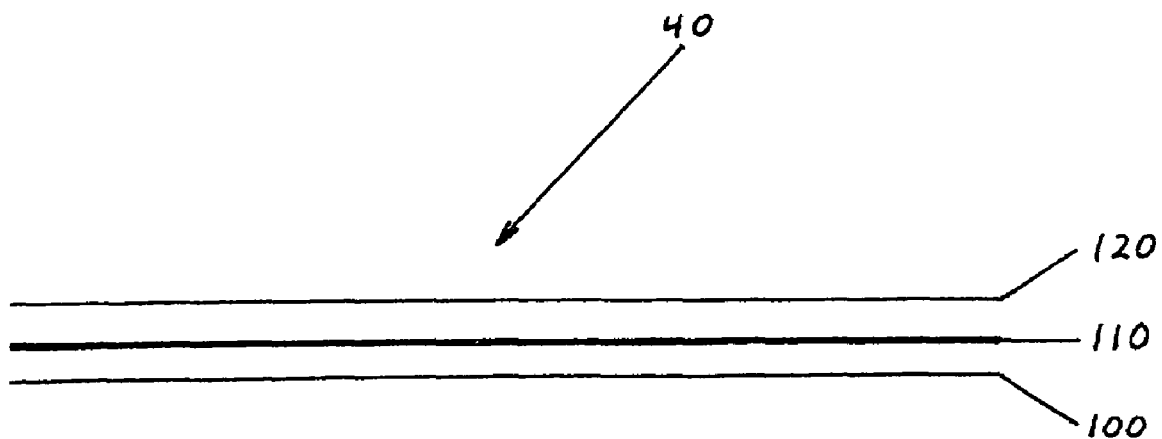
FIG. 4 is an exploded side view of a conductive substrate in accordance with one embodiment of the present invention.

Referring briefly to FIG. 4, the conductive substrate 40 includes three layers, the back side 120, a middle layer 110, and a front side 100. The back side 120 can be made of any metal conductive materials so that energy received from the conductive wire fan 55 is better dispersed across the surface area of the conductive substrate 40. The metal can be any conductive metal including silver, copper, tin, nickel, aluminum, chromium, cadmium, zinc, gold and platinum, preferably silver, gold, or platinum. The metal can be adhered to the middle layer 110 as a foil using an adhesive. Alternatively, the metal may also be dispersed in a solution that is then sprayed or printed onto the middle layer 110. Preferably, the back side 120 is a 0.3 mil layer of Ag (Silver) applied onto the middle layer 110 in the form of an ink by Prime Label & Screen of Pewaukee, Wis.

The middle layer 110 is a thin, flexible sheet of electrically conductive polymer film such as a graphite-filled polyvinyl chloride (PVC) film having a thickness between two and five mils. The middle layer 110 in the present embodiment is a graphite filled PVC film being 4 mil thick supplied by Prime Label & Screen.

The front side 100 is a conductive layer containing a conductive metal and a chloride of the conductive metal. As in the back side 120, the front side 100 can be in the form of a foil that is adhered to the middle layer 110 with an adhesive, or the front side 100 can be a solution containing dispersed metal and metal chloride particles. The metal and metal chloride may be separated into individual layers or merged together in the form of a coating or ink. As will be discussed in further detail below, the ratio of the metal and metal chloride along with the overall amount of metal and metal chloride are both important features of the present invention. The front side 100 of the present embodiment preferably includes a 1 mil layer of Ag/AgCl ink having a ratio of 65%/35% applied to the middle layer 110 by a coating operation.

A conductive hydrogel 30 is included adjacent to the front side 100. The conductive hydrogel 30, also known as a conductive polymer, is generally pliable and is naturally tacky. These features allow the conductive hydrogel 30 to conform to the patient's body and remain in contact over the entire surface area of the conductive hydrogel 30. Without the conductive hydrogel 30, energy current passing from the front side 100 to the patient's body is likely to be focused on small areas of contact causing burns in those locations. Additionally, the conductive hydrogel 30 contains a relatively large amount of water along with a salt so that electrical energy can pass easily between the front side 100 and the patient's skin. The actual reaction taking place will be discussed in further detail below. The conductive hydrogel 30 of the present embodiment contains 5% KCl and is a product made by ConMed Corporation, Utica, N.Y. under the name 2000.

Even though the remaining features of the MFE pad are not directly in the path of electrical energy, they will be discussed at this time. A strain relief 20 is added below the conductive hydrogel 30 in the area of the wire fan 55 of the conductive wire 50. The strain relief 20, is preferably made of a 1/32" polyethylene foam with an adhesive on both sides. The strain relief 20 disperses any loading placed on the conductive wire 50 and the wire fan 55 over a larger area of the MFE pad. The strain relief 20 has adhesive on both sides so that it adheres to a foam backing 70 and the conductive hydrogel 30 on one side and the patient's skin on the other. Because of this mechanical use, other types of foams and thickness can be used to make a similar result. The strain relief of the present embodiment is made by MacTac.

The foam backing 70 is larger in surface area than the conductive substrate 40 and the conductive hydrogel 30. The foam backing 70 has an adhesive on one side used to adhere it to the conductive substrate 40, the conductive hydrogel 30 and to the patient's skin where the foam backing 70 extends beyond the perimeter of the conductive hydrogel 30. The foam backing 70 is preferably made of a nonconductive material such as a polyethylene foam to protect the patient and any other users from a potential (unintentional) shock. The foam backing 70 may also function as a seal around the conductive hydrogel 30 to help reduce any drying of the hydrogel 30 that may occur during use. In this embodiment, the foam backing is made of a 1/16" polyethylene material supplied by MacTac.

It is further envisioned that the foam backing 70 may function as packaging surrounding and protecting the other components during shipment and storage prior to use. To this end, a release liner 10 having a surface area similar to the foam backing 70 may be included across the exposed surfaces of the conductive hydrogel 30, the strain relief 20, and the foam backing 70. The release liner 10 protects the adhesive qualities of each of these features from damage until the MFE pad is to be placed on a patient. The release liner 10 used in this embodiment is a silicone coated semi-rigid polyethylene terephthalate (PET) film that is well known in the art. The release liner 10 may also be any other material that will lightly adhere to the adhesives and conductive hydrogel 30 without damaging them during separation.

A pair of MFE pads may be placed together in an opposed manner with a release liner 10 placed in between. A pair of MFE pads assembled in this way for shipment and storage may be able to sufficiently seal the assembly so that no external foil packaging is required. Elimination of this packaging would significantly reduce the waste associated with the use of MFE pads.

Referring now to the functionality of the MFE pad, the individual components of the conductive substrate 40 and the conductive hydrogel 30 dictate the overall performance of the MFE pad during service. One of the key measurements of performance is outlined in the ANSI/AAMI DF2:1996 standard for defibrillation overload recovery after 60 minutes of pacing. This standard requires that an MFE pad pair retain a DC voltage offset value of less than 400 mV during 60 minutes on pacing. In more general terms, the MFE pad pair must be able to effectively dissipate energy to the patient rather than retaining a portion of the energy applied during pacing. The materials and composition of the front side 100 of the conductive substrate 40 and the conductive hydrogel 30 play a large role in the effective compliance with the ANSI/AAMI standard.

Figure 5:
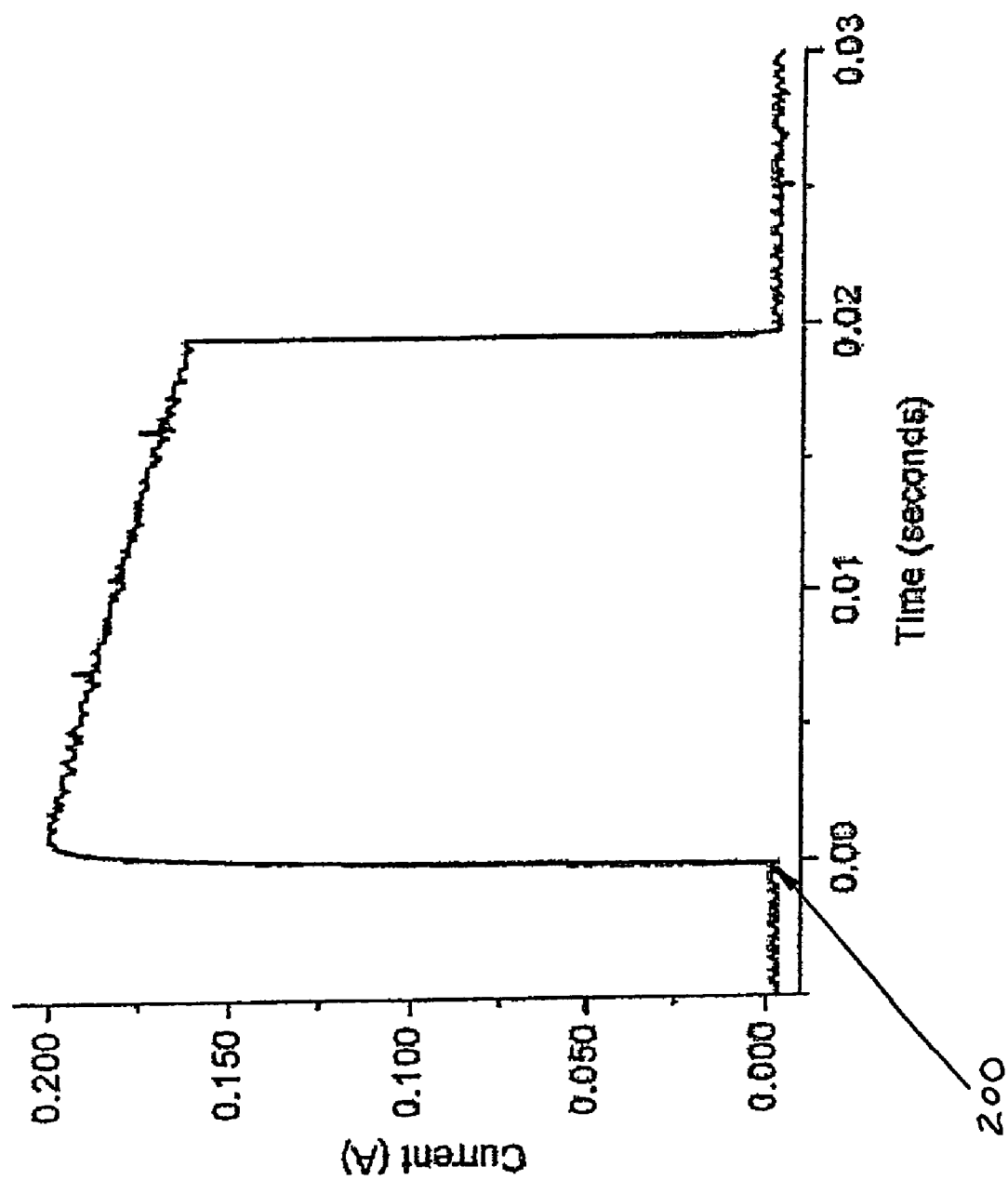
FIG. 5 is a graph showing an electrical waveform showing a current applied to a multifunction electrode pad during testing.

FIG. 5 shows a pacing waveform produced by a Physio-Control Lifepak 9P. The waveform shows that the Physio-Control Lifepak 9p creates a 200 mA pulse for 0.02 seconds. The Lifepak 9P is capable of producing this pulse at a maximum rate of 170 pulses per minute or 2.83 per second.

Figure 6:
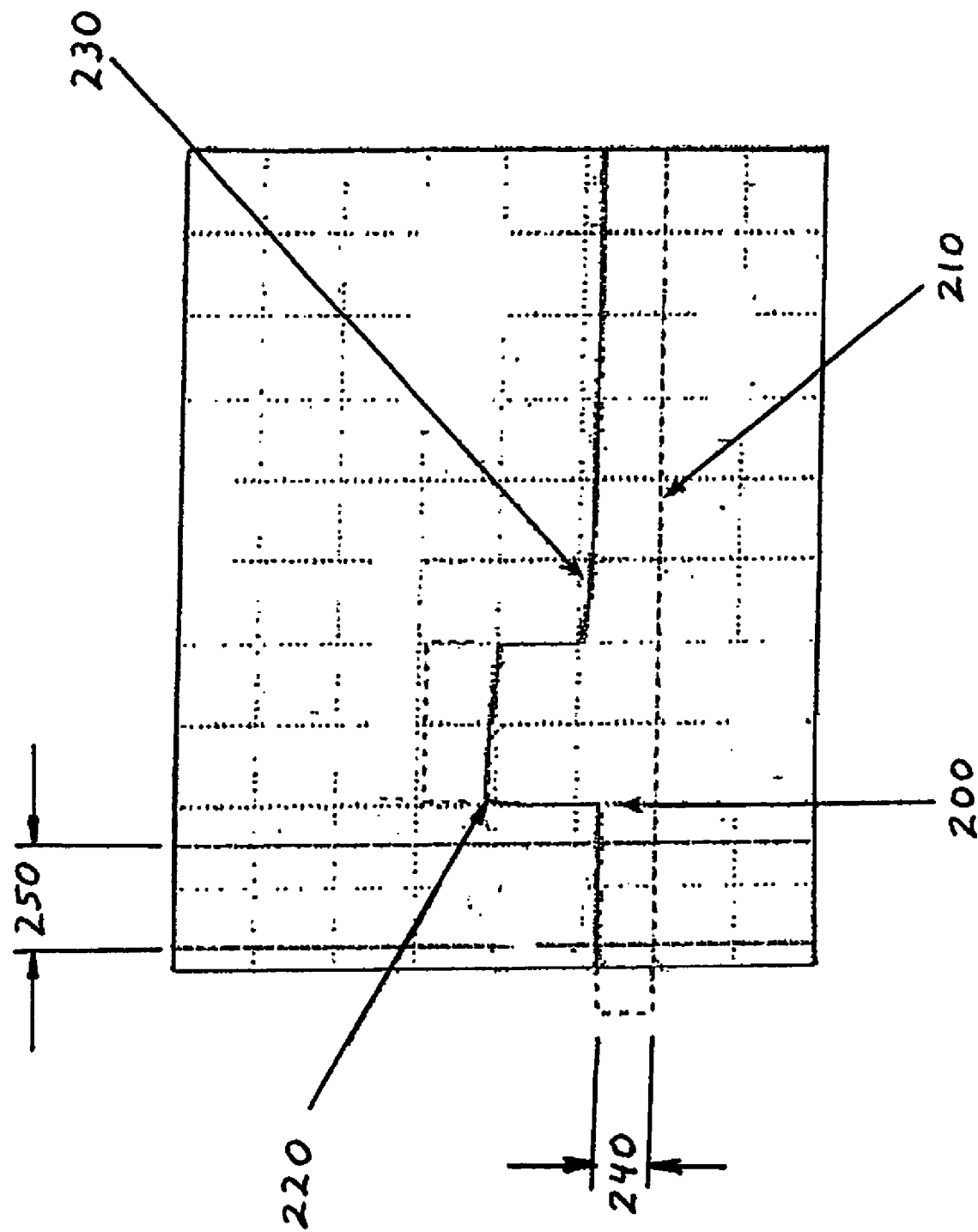
FIG. 6 is a graph showing an electrical waveform showing a voltage created across a pair of multifunction electrode pads during testing.

FIG. 6 shows the resulting voltage across an MFE pad pair according to the invention during pacing with constant 200 mA current pulses. For correlation with current output of the Lifepak 9P shown in FIG. 5, the beginning of the 200 mA current pulse 200 is the same start point 200 shown in FIG. 7. The pulse height 220 reflects the impedance Z of the MFE pad pair during pacing where Z=V0/200 mA and V0 is the pulse height above ground (0 V) 210. The voltage across the pad pair while no current is being supplied is shown as 230. A window 250 is set immediately before the next pacing current pulse is applied. The DC voltage offset 240 is measured during time window 250.

During pacing, one of the MFE pads functions as an anode where the positive current is transferred to the patient. The other pad in the MFE pair is, therefore, a cathode where the positive current of the electrical energy is passed out of the patient's body.

Chemical reactions within the MFE pad functioning as an anode differ from those occurring within the MFE pad functioning as the cathode. In the MFE pad functioning as the anode, the chloride ions from the conductive hydrogel 30 are combined with metal ions (e.g., Ag) on the front side 100 affecting a net gain of metal chloride on the front side 100 of the conductive substrate 40. The chemical reaction can be characterized as Ag_(aq)+Cl−(aq)=>AgCl(s). In the MFE pad functioning as the cathode, chloride ions from the metal chloride in the front side 100 are released resulting in a net loss of metal chloride in the front side 100 and "free" Ag+ and Cl− ions in the conductive hydrogel 30.

Most known MFE pads use a metal/metal chloride front side 100 having a ratio of metal to metal chloride between 95%/5% and 90%/10% and a thickness of typically around 1/3 mil. All of the MFE pads using the known structure and composition fail to pass the ANSI/AAMI standard requirements by generating excessive DC voltage offset 240. As referenced above, one method of passing the standard utilizes a front side where "the coating is considerably thicker by a factor of six. Because the ink in conventional products is about 1/3 mil thick, the thickness of the ink forming at least the central portion of the known pad is about 2 mils".

The present embodiment utilizes a much thinner and much less expensive front side 100 of the conductive substrate 40 that is also capable of meeting the ANSI/AAMI standard. The ratio of metal/metal chloride used in the front side 100 of the present embodiment differs greatly from the prior art to provide sufficient metal chloride for use during pacing. Three ⅓ mil coats using the metal/metal chloride ratio of 65%/35% allows the present invention to pass the ANSI/AAMI standard using much less metal and, therefore, much less cost.

Figure 7:
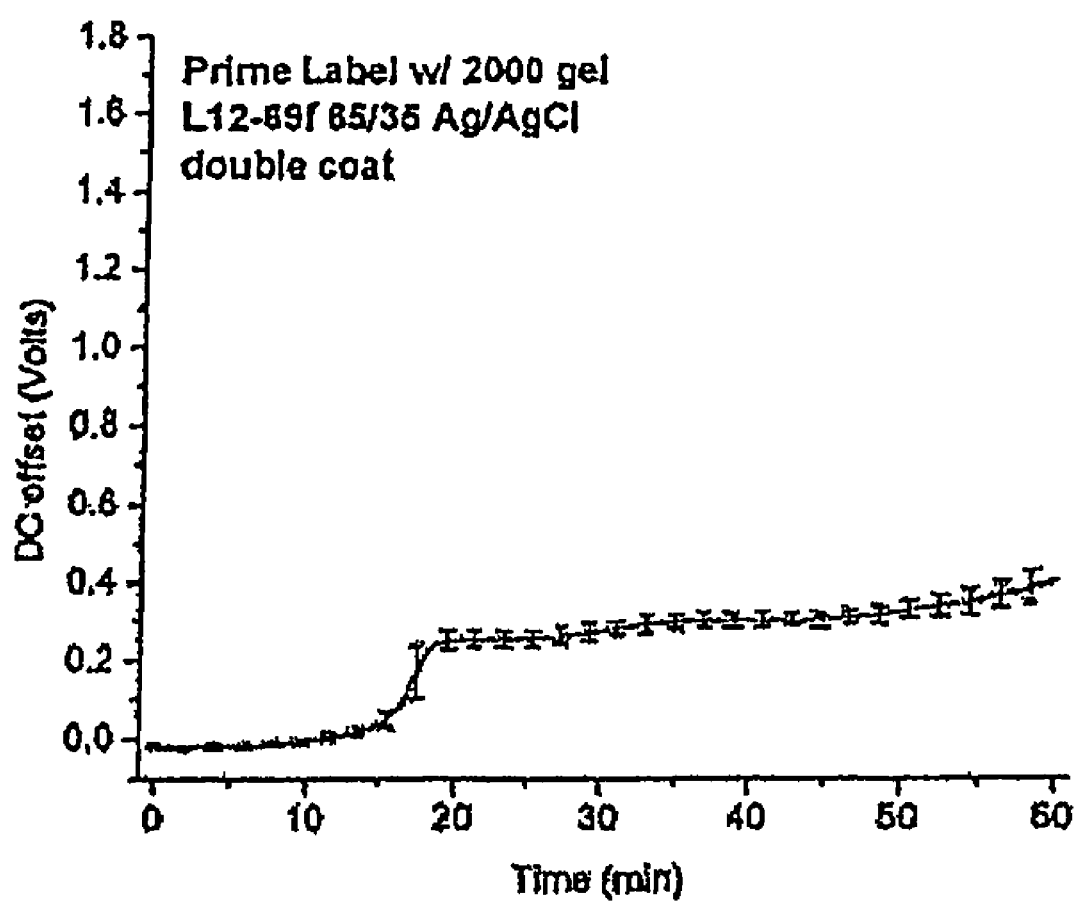
FIG. 7 is a graph showing the voltage created across a pair of multifunction electrode pads in accordance with one embodiment of the present invention during a 60 minute test.

An MFE pad pair utilizing a front side 100 of two ⅓ mil coats of a 65%/35% silver/silver chloride ink according to the present embodiment generated only 400 mV of DC voltage offset after 60 minutes of pacing. A graph of this validation test is shown in FIG. 7.

Variations of this preferred embodiment are also envisioned where an additional layer of the metal/metal chloride front side is applied to further enhance the duration for which the MFE pad pair will function within acceptable standards. Additionally, because this is exceptionally advantageous to the cathode portion of the electrode pair, it is also envisioned that only one of the MFE pads within the pad pair have a front side 100 with a metal/metal chloride ratio of 65%/35%. The other pad used as an anode may contain a cheaper or alternative front side 100, which may not function adequately as a cathode.

What is claimed:

1. A multifunction electrode pad comprising:
a multi-strand conductor having one end in the form of dispersed carbon fibers, and another end adapted for connection to a defibrillation unit;
a conductive substrate in electrical communication with said one end of said multi-strand conductor, said conductive substrate comprising a conductive back side, an intermediate conductive polymer layer, and a conductive front side, said front side being a metal/metal chloride coating containing at least 25% by weight of metal chloride;
a conductive hydrogel layer covering said front side of said conductive substrate; and a backing layer covering said one end of said multi-strand conductor and said back side of said conductive substrate, said backing layer having a surface area that is greater than the surface area of said conductive hydrogel layer.

2. A multifunction electrode of claim 1, wherein said metal chloride is present in said metal/metal chloride coating in an amount of not more than 45% by weight.

3. A multifunction electrode of claim 2, wherein the thickness of said front side of said conductive substrate ranges from about 0.6 to about 1.0 mils.

4. A multifunction electrode of claim 3, wherein said metal chloride is present in said metal/metal chloride coating in an amount of 30%-40% by weight.

5. A multifunction electrode of claim 4, wherein said metal chloride is present in said metal/metal chloride coating in an amount of 35% by weight.

6. A multifunction electrode of claim 2, wherein said metal/metal chloride coating contains a mixture of metal particles and metal chloride particles.

7. A multifunction electrode according to claim 6, wherein said metal particles comprise silver and said metal chloride particles comprise silver chloride.

8. A multifunction electrode of claim 1, wherein said conductive back side of said conductive substrate has a thickness of about 0.3 to about 1.0 mils.

9. A multifunction electrode of claim 1, wherein said conductive back side is a metal foil.

10. A multifunction electrode of claim 1, wherein said conductive back side is a metal/metal chloride coating.

11. A multifunction electrode of claim 10, wherein the composition of said conductive back side is the same as the composition of said conductive front side.

12. A stacked laminate comprising:
first and second multifunction electrodes, where each of the first and second multifunction electrodes comprises,
a multi-strand conductor having one end in the form of dispersed carbon fibers, and another end adapted for connection to a defibrillation unit,
a conductive substrate in electrical communication with said one end of said multi-strand conductor, said conductive substrate comprising a conductive back side, an intermediate conductive polymer layer, and a conductive front side, said front side being a metal/metal chloride coating containing at least 25% by weight of metal chloride,
a conductive hydrogel layer covering said front side of said conductive substrate, and
a backing layer covering said one end of said multi-strand conductor and said back side of said conductive substrate, said backing layer having a surface area that is greater than the surface area of said conductive hydrogel layer;
the first and second multifunction electrodes being positioned such that the conductive hydrogel layer of the first multifunction electrode faces the conductive hydrogel layer of the second multifunction electrode; and
a release layer having first and second sides on which the conductive hydrogel layers of the first and second multifunction electrodes are adhered, respectively,
wherein the backing layers of said first and second multifunction electrodes are also adhered to the first and second sides of the release layer to seal the conductive hydrogel layers from the environment.

* * * * *